(12) United States Patent
Schwartz et al.

(10) Patent No.: US 6,678,618 B1
(45) Date of Patent: Jan. 13, 2004

(54) NEURAL NETWORK METHODS TO PREDICT ENZYME INHIBITOR OR RECEPTOR LIGAND POTENCY

(75) Inventors: Steven D. Schwartz, Pelham, NY (US); Vern L. Schramm, New Rochelle, NY (US); Benjamin B. Braunheim, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/711,625

(22) Filed: Nov. 13, 2000

Related U.S. Application Data

(63) Continuation of application No. 09/100,741, filed on Jun. 19, 1998, now Pat. No. 6,185,548.

(51) Int. Cl.[7] .................. G01N 31/00; G01N 33/48; G06F 17/00; G06F 15/00
(52) U.S. Cl. ................... 702/27; 702/19; 706/45; 706/47; 712/200
(58) Field of Search ................ 702/27, 19; 706/45, 706/47; 712/200

(56) References Cited

PUBLICATIONS

Bohm, G, "New approaches in molecular–structure prediction," Biophysical Chemistry, 1996, vol. 59, No. 1–2, Abstract only.*
Brusic et al., "Prediction of MHC class II–binding peptides using an evolutionary algorithm and artificial neural network," Bioinformatics, 1998, vol. 14, No. 2, pp. 121–130.*
Bagdassarian et al., "Molecular Electrostatic Potential Analysis for Enzyme Substrates, Competitive Inhibitors, and Transition–State Inhibitors," 1996, vol. 118, pp. 8825–8836.*
Betts et al., Cytidine Deaminase. The 2–3 Angstrom Crystal Structure of an Enzyme:Transition–state Analog Complex. J. Mol. Biol., 235:635–56, 1994.
Ehrlich and Schramm, Electrostatic Potential Surface Analysis of the Transition State for AMP Nucleosidase and for Formycin 5'–Phosphate, a Transition–State Inhibitor. Biochem., 33:8890–96, 1994.
Frick et al., Binding of Pyrimidin–2–one Ribonucleoside by Cytidine Deaminase as the Transition–State Analogue 3,4–Dihydroouridine and the Contribution of the 4–Hydroxyl Group to Its Binding Affinity. Biochemistry, 28:9423–30, 1989.
Gasteiger et al., Representation of Molecular Electrostatic Potentials by Topological Feature Maps. J. Am. Chem. Soc., 116:4608–20, 1994.
Horenstein and Schramm, Electronic Nature of the Transition State for Nucleoside Hydrolase. A Blueprint for Inhibitor Design. Biochemistry, 32:7089–97, 1993.
Kline and Schramm, Electrostatic Potential Surfaces of the Transition State for AMP Deaminase and for (R)–Coformycin, a Transition State Inhibitor. J. Biol. Chem., 269:22385–90, 1994.
So and Richards, Application of Neural Networks: Quantitative Structure–Activity Relationships of the Derivatives of 2,4–Diamino–5–(substituted–benzyl) pyrimidines as DHFR Inhibitors. J. Med. Chem., 35:3201–7, 1992.
Wagener et al., Autocorrelation of Molecular Surface Properties for Modeling Corticosteroid Binding Globlulin and Cytosolic Ah Receptor Activity by Neural Networks. J. Am. Chem. Soc., 117:7769–75, 1995.
Weinstein et al., Predictive Statistics and Artificial Intelligence in the U.S. National Cancer Institute's Drug Discovery Program for Cancer and AIDS. Stem Cells, 12:13–22, 1994.

\* cited by examiner

*Primary Examiner*—Kenneth R. Horlick
*Assistant Examiner*—Young Kim
(74) *Attorney, Agent, or Firm*—Amster, Rothstein & Ebenstein LLP

(57) ABSTRACT

A new method to analyze and predict the binding energy for enzyme-transition state inhibitor interactions is presented. Computational neural networks are employed to discovery quantum mechanical features of transition states and putative inhibitors necessary for binding. The method is able to generate its own relationship between the quantum mechanical structure of the inhibitor and the strength of binding. Feed-forward neural networks with back propagation of error can be trained to recognize the quantum mechanical electrostatic potential at the entire van der Waals surface, rather than a collapsed representation, of a group of training inhibitors and to predict the strength of interactions between the enzyme and a group of novel inhibitors. The experimental results show that the neural networks can predict with quantitative accuracy the binding strength of new inhibitors. The method is in fact able to predict the large binding free energy of the transition state, when trained with less tightly bound inhibitors. The present method is also applicable to prediction of the binding free energy of a ligand to a receptor. The application of this approach to the study of transition state inhibitors and ligands would permit evaluation of chemical libraries of potential inhibitory, agonistic, or antagonistic agents. The method is amenable to incorporation in a computer-readable medium accessible by general-purpose computers.

2 Claims, 6 Drawing Sheets

NEURAL NETWORK METHODS TO PREDICT ENZYME INHIBITOR OR RECEPTOR LIGAND POTENCY

This is a continuation of application Ser. No. 09/100,741, filed Jun. 19, 1998, now U.S. Pat. No. 6,185,548, the contents of which is hereby incorporated by reference in its entirety.

This invention was made with United States government support under Grant NIH GM41916 from the NIH. The United States Government may have certain rights in this invention.

BACKGROUND OF THE INVENTION

The present invention relates to a method for calculating the binding free energy for interactions between biomolecules. More particularly, the present invention relates to a method that employs computational neural networks to discover quantum mechanical features of enzyme active site transition states, as well as quantum mechanical features required for binding of putative enzyme inhibitors. The present method is also applicable to discovering quantum mechanical features required for the binding of a potential ligand to a biological receptor. Computer-readable media may be incorporated with information enabling the method of the present invention to be performed on a general-purpose computer.

Enzymatically catalyzed reactions are characterized by geometric and electrostatic distortions of a substrate molecule into a transition state. The formation and stabilization of these transition states by enzymes are accompanied by increases in the rate of catalysis on the order of $10^{10}$–$10^{15}$ times faster than the uncatalyzed reaction. It is thought that an enzyme binds the transition state of a substrate molecule more tightly than either the substrate or the product. As a result, chemically stable molecules that mimic the substrate transition state should be potent inhibitors of enzyme activity.

The de novo design of transition state inhibitors requires accurate models of the enzyme-stabilized transition state. Advances in theory and computational chemistry have produced good models of stable molecules and enzymatic transition states from kinetic isotope effect experiments. However, the development of computational and theoretical methods of prediction of the binding constant of a putative inhibitor, prior to synthesis, would facilitate the discovery of novel inhibitors. These methods could be used to search chemical libraries for transition state mimics.

There is a long history of the development of methods to predict the binding of biological agents to enzymes or receptors. The methods generally fall into one of two categories. The first is the use of docking or molecular dynamics studies to investigate the interactions of substrates with a variety of biological molecules, such as enzymes or receptor sites. The second is the use of Quantitative Structure Activity Relations (hereinafter "QSARs"), which usually investigate the properties of potential therapeutic agents in the absence of their biological target. Each of these methods have advantages and disadvantages.

The concept of docking or molecular dynamics studies is that application of physical laws of motion or static interaction can be applied to biological systems to predict the strength of interaction of a substrate with a complex biological molecule. In general, biological macromolecules and their substrates form a system too large for ab initio quantum chemical methods to be used to generate electronic potential energies, and so parametrized classical force fields are employed on which classical mechanics simulations can be run. This is a massive technology with an equally huge literature. A variety of algorithms have been developed with allow efficient integration of Newton's equations. In addition, Monte Carlo methods are of critical importance in this field. There have also been recent advances in mixing quantum and classical mechanics, such as the surface hopping methods in chemical physics. Because even this calculation is challenging for complex systems, static methods, which treat parts of a system as dielectric continua, have been employed. These approaches have been employed in docking studies, in which substrates are virtually oriented and bound to an active site of an enzyme or other biomolecule.

As important as these approaches are, there are still difficulties in the application of these approaches to drug design and analysis. First, there are a great many approximations inherent in the development of force field and dielectric continua models. Though these methods have been studied for many years, it is still difficult to know which approximations are appropriate. Second, these calculations are difficult to perform, even when the approximations-are appropriately employed, and require significant computer resources. As a result, the use of such docking studies in searches of libraries of potential candidate drugs for interactions with a particular target enzyme is impractical. Third, a structure for the biomolecule of interest is required for these docking studies. If, for example, only a DNA sequence is available, these methods cannot be employed.

The second method for predicting biological activity, QSARs, focuses on the substrate molecule. The concept assumes that there is a database of experimental evidence from which inferences can be drawn as to the effectiveness of other molecules. Specific properties of substrate molecules, such as hydrophobicity, the presence of certain groups, steric parameters,etc., are empirically fit to experimentally determined biological activities. The assumption is that once this fitting is appropriately performed, an accurate prediction of biological activity of a previously untested molecule can be made by examining the molecule for the same properties. These predictions have become quite sophisticated, and structural parameters used gave been expanded to include quantum mechanical features of substrates such as electrostatic potential surfaces. For example, point-by-point comparison of quantum mechanical electrostatic potentials on molecular van der Waals surfaces has been used to predict inhibition constants for transition state inhibitors for the reaction catalyzed by AMP deaminase and AMP nucleosidase. While these approaches are powerful, there are a number of difficulties. First, one must be able to identify a specific feature that determines bioactivity. When multiple features are involved, it is difficult to determine how the interactions of these features affects bioactivity. Second, a single QSAR may not be able to identify bioactivity trends when a number of different mechanisms are present (as where, for example, an enzyme protonates some substrates but not others). Finally, in addition to the practical prediction of bioactivity among libraries of potentially bioactive compounds, it is desirable to develop a theoretical approach that can help identify the features of the candidate molecules that are important, and thereby help to elucidate unknown mechanisms in the bioactivity.

The present invention is based on prior work on molecular similarity measures which compare electrostatic potential surfaces on the van der Waals surface of two different molecules. Two different molecules having similar electrostatic potentials have been found to have similar binding properties. Therefore, strong electrostatic similarity to an experimentally determined transition state result in strong binding, and a powerful transition state inhibitor. The similarity measure is defined as follows:

$$S_e = \frac{\sum_{i=1}^{nA}\sum_{j=1}^{nB} \varepsilon_i^A \varepsilon_j^B \exp(-\alpha r_{ij}^2)}{\sqrt{\sum_{i=1}^{nA}\sum_{j=1}^{nA} \varepsilon_i^A \varepsilon_j^A \exp(-\alpha r_{ij}^2)} \times \sqrt{\sum_{i=1}^{nB}\sum_{j=1}^{nB} \varepsilon_i^B \varepsilon_j^B \exp(-\alpha r_{ij}^2)}}$$

wherein $\varepsilon_i^A$ is an electrostatic potential on molecule A at position i, $\varepsilon_i^B$ is an electrostatic potential on molecule B at position i, $r_{ij}$ is a distance between points i and j on a surface, and $\alpha$ is a decay constant employed so that points that are very far apart do not strongly affect the similarity measure. The similarity measures were first applied to transition state inhibitors for the reactions catalyzed by AMP deaminase, adenosine deaminase, and AMP nucleosidase. Transition state structures for each enzyme were obtained by kinetic isotope experiments (Kline et al., J. Biol Chem. 269:22385–22390(1994); Ehrlich et al., Biochem. 33:8890–8896 (1994)). Electrostatic potentials were then calculated for the transition states, the substrates, and the putative inhibitors. These were obtained using the GAUSSIAN 94 quantum chemistry package (from Gaussian, Inc., Pittsburgh, Pa.). Minimal basis sets (STO3G) were used in the initial studies, and were thereafter confirmed using higher order basis sets. The molecules were oriented with respect to each other to maximize geometric overlap, and the electrostatic similarities were calculated.

For these simple reactions, the calculated numerical similarity was a reasonable predictor of binding free energy. FIG. 1 shows a plot of experimentally determined binding free energy versus electrostatic similarity (Se) for the AMP nucleosidase reaction and for three transition state inhibitors. The three inhibitors fall reasonably closely to a line defined by connecting the binding free energy versus Se for the substrate AMP and the transition state. Similarly, FIG. 2 shows a plot of experimentally determined binding free energy versus electrostatic similarity for adenosine deaminase. One transition state inhibitor, 1,6-dihydropurine ribonucleoside is a significant outlier, but the remaining results are quite good.

Despite these encouraging initial results, it soon became apparent that the similarity measure does not accurately predict all cases of inhibitor enzyme binding. The reason is that the Se treats all points on the van der Waals surface equivalently. It is thus quite possible to have a perfect configuration for binding in the region of an inhibitor molecule that interacts with the active site, but have significant differences remote from this site. As a result, the similarity measure would produce a result that would predict weaker binding than the actual binding free energy. Similarly, a molecule that initially looks very different from a transition state inhibitor could be changed electrostatically by its interaction with the enzyme, by e.g., protonation, to a form that might have a high binding free energy. Again, the similarity measure would predict a weaker binding than what would be measured experimentally. Furthermore, there are many reasonable algebraic similarity measures that may be applied in each cases and choosing the most appropriate measure would require extensive computational resources.

An artificial neural network is a computer algorithm which, during a training process, can learn features of input patterns and associate these with an output. After the learning phase is completed, the trained network enables the computer to predict an output for a pattern not included in the training process. Neural networks have been used in a small number of cases to study biological activity prediction. For example, Kohonen self-organizing organizing maps have been used to transform the three-dimensional surface of biomolecules to a two-dimensional projection (Gasteiger et al., J. Am. Chem. Soc. 116:4608–4620 (1994)). Similarly, the molecular electrostatic potential at the van der Waals surface has been collapsed onto a series of 12 autocorrelation coefficients, and these were used in a neural network (Wagener et al., J. Am. Chem. Soc. 117:7769–7775 (1995)). In both these cases, potentially useful data were discarded as the three-dimensional surface information was converted to a two-dimensional representation. Neural networks have also been used to predict the mode of action of chemotherapeutic agents (Weinsteinet al., Stem Cells 12:13–22 (1994)). Finally, neural networks have been used to predict biological activity from discrete QSAR descriptions of molecular structure (So and Richards, J. Med. Chem. 35:3201–3207 (1992)). However, this approach fails if the correct QSAR is not selected.

It is therefore desirable to have a method that can accurately predict binding free energy for a wide variety of potential inhibitors. It is also desirable to have a method for determination of binding free energy that identifies those regions of a potential inhibitor or other bioactive molecule that are especially important in binding, and thereby help elucidate unknown binding features. Furthermore, it is desirable to have a method for determining binding free energy that would adjust itself in each case to the form most suited to that particular case.

SUMMARY AND OBJECTS OF THE INVENTION

Accordingly, it is an object of the present invention to overcome the limitations of the prior art.

It is another object of the present to provide a method for determining the free energy of binding of a substrate of known structure to an enzyme.

It is another object of the present invention to provide a method for determining the free energy of binding of an inhibitor of known structure to an enzyme.

It is another object of the present invention to provide a method for determining the free energy of binding of a ligand to a receptor.

It is another object of the present invention to provide a computer-readable medium encoded with information that enables a general purpose computer to perform the method of the present invention.

Briefly stated, a new method to analyze and predict the binding energy for enzyme-transition transition state inhibitor interactions is presented. Computational neural networks are employed to discovery quantum mechanical features of transition states and putative inhibitors necessary for binding. The method is able to generate its own relationship between the quantum mechanical structure of the inhibitor and the strength of binding. Feed-forward neural networks with back propagation of error can be trained to recognize the quantum mechanical electrostatic potential at the entire van der Waals surface, rather than a collapsed representation, of a group of training inhibitors and to predict the strength of interactions between the enzyme and a group of novel inhibitors. The experimental results show that the neural networks can predict with quantitative accuracy the binding strength of new inhibitors. The method is in fact able to predict the large binding free energy of the transition state, when trained with less tightly bound inhibitors. The present method is also applicable to prediction of the binding free energy of a ligand to a receptor. The application of this approach to the study of transition state inhibitors and ligands would permit evaluation of chemical libraries of potential inhibitory, agonistic, or antagonistic agents. The method is amenable to incorporation in a computer-readable medium accessible by general-purpose computers.

According to an embodiment of the present invention, a method for determining the free energy of binding of a potential ligand to a receptor comprises the steps of obtaining, for each of two or more actual receptor ligands, at least one of a structure and a free energy of binding to the receptor, such that each of the two or more actual receptor ligands has a known structure and a known free energy of binding to the receptor, orienting the structures of the two or more actual receptor ligands for maximum geometric coincidence with each other, determining an electrostatic potential at each of more than one point on a van der Waals surface of each of the actual receptor ligands, thereafter, mapping each of the electrostatic potentials of each of the actual receptor ligands onto a geometric surface of one of the two or more actual receptor ligands, each of the two or more actual receptor ligands being thereby described by an identical surface geometry but a different electrostatic potential surface, and each of the electrostatic potentials being described by positional information relating the electrostatic potentials to the geometric surface, thereafter, inputting the electrostatic potentials, the positional information, and the known free energy of binding of one of the two or more actual receptor ligands into a neural network, thereafter, training the neural network until the neural network predicts the free energy of binding of the one of the two or more actual receptor ligands, repeating the steps of inputting and training for each of the remaining the two or more actual receptor ligands to produce a trained network, thereafter, determining a potential ligand electrostatic potential at each of more than one point on a van der Waals surface of the potential ligand, the potential ligand having a known structure and an unknown free energy of binding to the receptor, orienting the structure of the potential ligand for maximum geometric coincidence with the structures of the two or more actual receptor ligands, thereafter, mapping each of the electrostatic potentials of the potential ligand onto a geometric surface of one of the two or more actual receptor ligands, the potential ligand having a surface geometry identical to that of the two or more actual receptor ligands, but a different electrostatic potential surface, and each of the electrostatic potentials of the potential ligand being described by positional information relating the electrostatic potentials to the geometric surface, thereafter, inputting the electrostatic potentials and the positional information of the electrostatic potentials of the potential ligand into the trained network, and using the trained network to calculate a free energy of binding of the potential ligand to the receptor.

According to another embodiment of the present invention, a method for determining the free energy of binding of a potential ligand to a receptor comprises the steps of obtaining a structure for the potential ligand, orienting structures of two or more actual receptor ligands for the receptor for maximum geometric coincidence with each other, each of the two or more actual receptor ligands having a known structure and a known free energy of binding to the receptor, determining an electrostatic potential at each of more than one point on a van der Waals surface of each of the actual receptor ligands, thereafter, mapping each of the electrostatic potentials of each of the actual receptor ligands onto a geometric surface of one of the two or more actual receptor ligands, each of the two or more actual receptor ligands being thereby described by an identical surface geometry but a different electrostatic potential surface, and each of the electrostatic potentials being described by positional information relating the electrostatic potentials to the geometric surface, thereafter, inputting the electrostatic potentials, the positional information, and the known free energy of binding of one of the two or more actual receptor ligands into a neural network, thereafter, training the neural network until the neural network predicts the free energy of binding of the one of the two or more actual receptor ligands, repeating the steps of inputting and training for each of the remaining the two or more actual receptor ligands to produce a trained network, thereafter, determining an potential ligand electrostatic potential at each of more than one point on a van der Waals surface of the potential ligand, the potential ligand having an unknown free energy of binding to the receptor, orienting the structure of the potential ligand for maximum geometric coincidence with the structures of the two or more actual receptor ligands, thereafter, mapping each of the electrostatic potentials of the potential ligand onto a geometric surface of one of the two or more actual receptor ligands, the potential ligand having a surface geometry identical to that of the two or more actual receptor ligands, but a different electrostatic potential surface, and each of the electrostatic potentials of the potential ligand being described by positional information relating the electrostatic potentials to the geometric surface, thereafter, inputting the electrostatic potentials and the positional information of the electrostatic potentials of the potential ligand into the trained network, and using the trained network to calculate a free energy of binding of the potential ligand to the receptor.

According to another embodiment of the present invention, a computer readable medium comprises computer-readable information, the information capable of interacting with a computer to produce an output, the output being a calculated free energy of binding of a potential ligand to a receptor, the output being calculated by orienting structures of the two or more actual receptor ligands for maximum geometric coincidence with each other, each of the two or more actual receptor ligands having a known structure and a known free energy of binding to the receptor, determining an electrostatic potential at each of more than one point on a van der Waals surface of each of the actual receptor ligands, thereafter, mapping each of the electrostatic potentials of each of the actual receptor ligands onto a geometric surface of one of the two or more actual receptor ligands, each of the two or more actual receptor ligands being thereby described by an identical surface geometry but a different electrostatic potential surface, and each of the electrostatic potentials being described by positional information relating the electrostatic potentials to the geometric surface, thereafter, inputting the electrostatic potentials, the positional information, and the known free energy of binding of one of the two or more actual receptor ligands into a neural network, thereafter, training the neural network until the neural network predicts the free energy of binding of the one of the two or more actual receptor ligands, repeating the steps of inputting and training for each of the remaining the two or more actual receptor ligands to produce a trained network, thereafter, determining an potential ligand electrostatic potential at each of more than one point on a van der Waals surface of the potential ligand, the potential ligand having a known structure and an unknown free energy of binding to the receptor, orienting the structure of the potential ligand for maximum geometric coincidence with the structures of the two or more actual receptor ligands, thereafter mapping each of the electrostatic potentials of the potential ligand onto a geometric surface of one of the two or more actual receptor ligands, the potential ligand having a surface geometry identical to that of the two or more actual receptor ligands, but a different electrostatic potential surface, and each of the electrostatic potentials of the potential ligand being described by positional information relating the electrostatic potentials to the geometric surface, thereafter, inputting the electrostatic potentials and the positional information of the electrostatic potentials of the potential ligand into the trained network, and using the trained network to calculate a free energy of binding of the potential ligand to the receptor.

According to another embodiment of the present invention, a method for determining a free energy of binding of a potential transition-state inhibitor to an enzyme comprises the steps of obtaining, for each of two or more enzyme substrates or inhibitors, at least one of a structure and a free energy of binding to the enzyme, such that each of the two or more enzyme substrates or inhibitors has a known structure and a known free energy of binding to the enzyme, orienting the structures of the two or more enzyme substrates or inhibitors for maximum geometric coincidence with each other, determining an electrostatic potential at each of more than one point on a van der Waals surface of each of the enzyme substrates or inhibitors, thereafter, mapping each of the electrostatic potentials of each of the enzyme substrates or inhibitors onto a geometric surface of a transition state inhibitor, each of the enzyme substrates or inhibitors being thereby described by an identical surface geometry but a different electrostatic potential surface, and each of the electrostatic potentials being described by positional information relating the electrostatic potentials to the geometric surface of the transition state inhibitor, thereafter, inputting the electrostatic potentials, the positional information, and the known free energy of binding of one of the two or more enzyme substrates or inhibitors into a neural network, thereafter, training the neural network until the neural network predicts the free energy of binding of the one of the two or more enzyme substrates or inhibitors, repeating the steps of inputting and training for each of the remaining the two or more enzyme substrates or inhibitors to produce a trained network, thereafter, determining an potential transition electrostatic potential at each of more than one point on a van der Waals surface of the potential transition-state inhibitor, the potential transition-state inhibitor having a known structure and an unknown free energy of binding to the enzyme, orienting the structure of the potential transition-state inhibitor for maximum geometric coincidence with the structures of the two or more enzyme substrates or inhibitors, thereafter, mapping each of the electrostatic potentials of the potential transition-state inhibitor onto a geometric surface of one of the two or more two or more enzyme substrates or inhibitors, such that the potential transition-state inhibitor has a surface geometry identical to that of the two or more actual receptor transition-state inhibitors, but a different electrostatic potential surface, and each of the electrostatic potentials of the potential transition-state inhibitor is described by positional information relating the electrostatic potentials to the geometric surface of the two or more enzyme substrates or inhibitors, thereafter, inputting the electrostatic potentials and the positional information of the electrostatic potentials of the potential transition-state inhibitor into the trained network, and using the trained network to calculate a free energy of binding of the potential transition-state inhibitor to the enzyme.

According to another embodiment of the present invention, a method for determining the free energy of binding of a potential transition-state inhibitor to a enzyme comprises the steps of obtaining a structure for the potential transition-state inhibitor, orienting structures of two or more enzyme substrates or inhibitors for the enzyme for maximum geometric coincidence with each other, each of the two or more enzyme substrates or inhibitors having a known structure and a known free energy of binding to the enzyme, determining an electrostatic potential at each of more than one point on a van der Waals surface of each of the enzyme substrates or inhibitors, thereafter, mapping each of the electrostatic potentials of each of the enzyme substrates or inhibitors onto a geometric surface of one of the two or more enzyme substrates or inhibitors, each of the two or more enzyme substrates or inhibitors being thereby described by an identical surface geometry but a different electrostatic potential surface, and each of the electrostatic potentials being described by positional information relating the electrostatic potentials to the geometric surface, thereafter, inputting the electrostatic potentials, the positional information, and the known free energy of binding of one of the two or more enzyme substrates or inhibitors into a neural network, thereafter, training the neural network until the neural network predicts the free energy of binding of the one of the two or more enzyme substrates or inhibitors, repeating the steps of inputting and training for each of the remaining the two or more enzyme substrates or inhibitors to produce a trained network, thereafter, determining an potential transition-state inhibitor electrostatic potential at each of more than one point on a van der Waals surface of the potential transition-state inhibitor, the potential transition-state inhibitor having an unknown free energy of binding to the enzyme, orienting the structure of the potential transition-state inhibitor for maximum geometric coincidence with the structures of the two or more enzyme substrates or inhibitors, thereafter, mapping each of the electrostatic potentials of the potential transition-state inhibitor onto a geometric surface of one of the two or more enzyme substrates or inhibitors, the potential transition-state inhibitor having a surface geometry identical to that of the two or more enzyme substrates or inhibitors, but a different electrostatic potential surface, and each of the electrostatic potentials of the potential transition-state inhibitor being described by positional information relating the electrostatic potentials to the geometric surface, thereafter, inputting the electrostatic potentials and the positional information of the electrostatic potentials of the potential transition-state inhibitor into the trained network, and using the trained network to calculate a free energy of binding of the potential transition-state inhibitor to the enzyme.

According to another embodiment of the present invention, a computer readable medium comprises computer-readable information, the information capable of interacting with a computer to produce an output, the output being a calculated free energy of binding of a potential transition-state inhibitor to a enzyme, the output being calculated by orienting structures of the two or more actual receptor ligands for maximum geometric coincidence with each other, each of the two or more actual ligands having a known structure and a known free energy of binding to the enzyme, determining an electrostatic potential at each of more than one point on a van der Waals surface of each of the enzyme substrates or inhibitors, thereafter, mapping each of the electrostatic potentials of each of the enzyme substrates or inhibitors onto a geometric surface of one of the two or more enzyme substrates or inhibitors, each of the two or more enzyme substrates or inhibitors being thereby described by an identical surface geometry but a different electrostatic potential surface, and each of the electrostatic potentials being described by positional information relating the electrostatic potentials to the geometric surface, thereafter, inputting the electrostatic potentials, the positional information, and the known free energy of binding of one of the two or more enzyme substrates or inhibitors into a neural network, thereafter, training the neural network until the neural network predicts the free energy of binding of the one of the two or more enzyme substrates or inhibitors, repeating the steps of inputting and training for each of the remaining the two or more enzyme substrates or inhibitors to produce a trained network, thereafter, determining an potential transition-state inhibitor electrostatic potential at each of more than one point on a van der Waals surface of the potential receptor ligand, the potential receptor ligand having a known structure and an unknown free energy of binding to the enzyme, orienting the structure of the potential transition-state inhibitor for maximum geometric coincidence with the structures of the two or more enzyme substrates or inhibitors, thereafter, mapping each of the electrostatic potentials of the potential transition-state inhibitor onto a geometric surface of one of the two or more enzyme substrates or inhibitors, the potential transition-state inhibitor having a surface geometry identical to that of the two or more enzyme substrates or inhibitors, but a different electrostatic potential surface, and each of the electrostatic potentials of the potential transition-state inhibitor being described by positional information relating the electrostatic potentials to the geometric surface, thereafter, inputting the electrostatic potentials and the positional information of the electrostatic potentials of the potential transition-state inhibitor into the trained network, and using the trained network to calculate a free energy of binding of the potential transition-state inhibitor to the enzyme.

Additional advantages of the present invention will be apparent from the description which follows.

DESCRIPTION OF THE PREFERRED EMBODIMENTS

Figure 1:
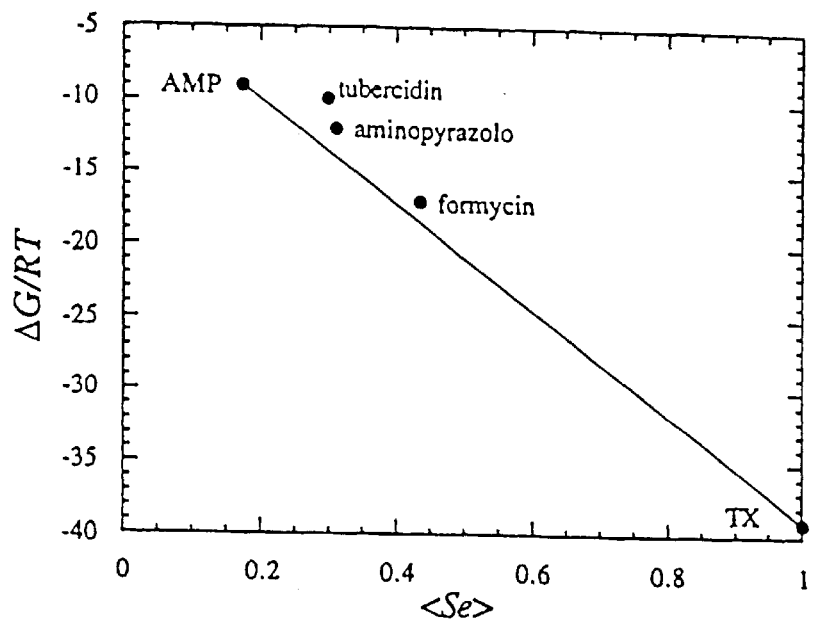
FIG. 1 shows a plot of the binding free energy ($\Delta G/RT$) for AMP nucleosidase versus similarity measure (Se) according to the prior art.
Figure 2:
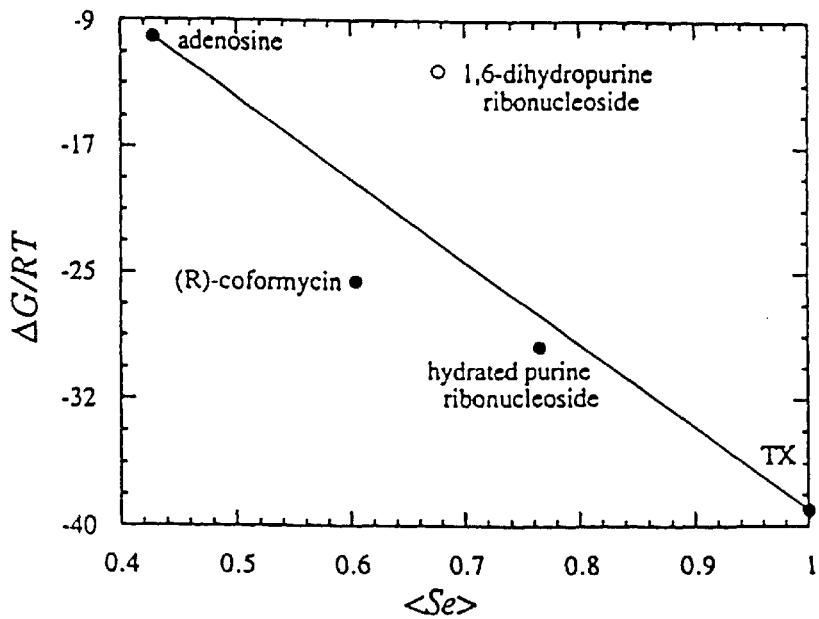
FIG. 2 shows a plot of the binding free energy ($\Delta G/RT$) for adenosine deaminase versus similarity measure (Se) according to the prior art.

To overcome the above-described limitations, the present inventors have tested the ability of computational neural networks to predict binding free energy. Neural networks are employed to investigate the properties of substrate and inhibitor molecules. Through training algorithms that are described below, the network can find properties and areas of molecules that are necessary for biological recognition, binding and action. The molecules are described using general quantum mechanical descriptions of the substrate and inhibitor molecules, and so the algorithm in a real sense "chooses its own QSAR". Because the method focuses on substrates and inhibitors, and because these molecules are small enough for application of standard quantum chemistry molecular orbital calculations, there is no ambiguity as to choice of force fields, dielectric constants, or classical versus quantum mechanics. In addition, complex problems associated with the binding of water and counter ions in active sites are also avoided. These constructions have been shown to be able to satisfy all the requirements for flexibility described above. That is, they are able to discern from input data the specific data crucial for forming the proper conclusion; and from the data are able to extrapolate to a relationship between input and output.

In the present work, the electrostatic potential at the van der Waals surface of a molecule is used as the physicochemical descriptor. The entire surface for each molecule, represented by a discrete collection of points, serves as the input to the neural network. To preserve the geometric and electrostatic integrity of the training molecules, a collapse onto a lower dimensional surface is avoided. After alignment of the inhibitor molecule for maximal geometrical overlap with the transition state structure, the electrostatic potentials on the inhibitor surface are mapped onto the van der Waals surface of the transition state. Therefore, though an inhibitor molecule takes on the geometry of the transition state, the electrostatic potentials decorating that surface are derived from the inhibitor itself.

The molecular electrostatic potential calculated at the van der Waals surface of the molecules is used as a descriptor of chemical structure and properties. Such information sheds light on the kinds of interactions a given molecule can have with the active site. Regions with electrostatic potentials close to zero are likely to be capable of van der Waals interactions. Regions with a partial positive or negative charge can serve as hydrogen bond donor or acceptor sites. Regions with even greater positive or negative potentials may be involved in coulombic interactions. The electrostatic potential also conveys information concerning the likelihood that a particular region can undergo electrophilic or nucleophilic attack.

The electrostatic potential surfaces are quantified as follows. After a constrained energy minimization of a molecular structure using the GAUSSIAN 94 package (GAUSSIAN 94, Revision C.2, Gaussian, Inc., Pittsburgh, Pa.), its CUBE function is used to calculate the electron density and electrostatic potential. Since molecules described by quantum mechanics have a finite electron density in all space, a reasonable cutoff is required to define a molecular geometry. One can closely approximate the van der Waals surface by finding all points around a molecule where the electron density is close to $0.002\pm\beta$ electron/bohr. $\beta$ is the acceptance tolerance since no Gaussian output will have an electron density of 0.002 exactly. The set of points thus generated will describe a surface under which approximately 95% of the electron density resides. $\beta$ is adjusted so that 17 points per atom are accepted, creating a fairly uniform molecular surface as shown previously (Bagdassarian et al., J. Amer. Chem. Soc. 118:8825–8836 (1996)). The information about a given molecular surface is described by a matrix with dimensions of 4×n where n is the number of points for the molecule, and the row vector of length 4 contains the x, y, z-coordinates of a given point and the electrostatic potential there.

For input of the surface features of the structures into a neural network the molecules must be oriented for maximum geometric coincidence. This can be done in either of two ways. In the first, the molecular stick figures are superimposed via, for example, the algorithms provide in the Insight II package (Biosym Technologies, San Diego, calif.). One selects the obvious atoms from two molecules that are to coincide spatially, which is a simple matter for molecules sharing a great deal of backbone similarity. Once the superposition is achieved, the GAUSSIAN calculations are performed with the NOSYMM feature to preserve the spatial orientations of the molecules. Only then are the surfaces constructed from the electrostatic potential and electron density outputs.

The second way to achieve properly oriented surfaces is as follows. Once the van der Waals surfaces of the molecules have been constructed through the procedure described above, two molecules are spatially positioned with their geometric centers at the coordinate origin. One molecule is held fixed while the other is rotated around its center, and for each new position a geometric similarity measure $S_g$ is used to gauge the degree of alignment:

$$S_g = \frac{\sum_{i=1}^{nA} \sum_{j=1}^{nB} \exp(-\alpha r_{ij}^2)}{\sqrt{\sum_{i=1}^{nA} \sum_{j=1}^{nA} \exp(-\alpha r_{ij}^2)} \sqrt{\sum_{i=1}^{nB} \sum_{j=1}^{nB} \exp(-\alpha r_{ij}^2)}}$$

The double sum in the numerator is over all surface points on molecule A and on molecule B. nA and nB refer to the number of surface points in molecule A and B, respectively. $r^2_{ij}$ is the spatial distance squared between point i on A and j on B. $\alpha$ is the length scale that weighs the degree to which spatial distances between i and j affect $S_g$. The denominator is a normalizing factor. $S_g$ is calculated for many random orientations, and the relative orientation with the maximum $S_g$ is saved as it corresponds to the orientation of molecule A with respect to B with maximal surface coincidence. All molecules are thus oriented to a reference target molecular surface—that of the transition state.

Input patterns entering into a neural network are presented in the form of a vector with entries $(l_1, l_2, \ldots, l_n)$. Since the molecules are represented by a 4×n matrix, a method is needed to discard the x,y,z-coordinates but maintain the electrostatic potentials while preserving the maximum amount of spatial information. This is accomplished by mapping the surface points of every molecule onto the same geometrical surface, such as, for example, that defined by the transition state (Bagdassarian et al., Int. J. Quant. Chem.; Quant. Biol Symp. 23:73–80 (1996)). In order to represent different molecules to the neural network, with their differences and similarities preserved, a nearest neighbor mapping function for the surface points is used. To accomplish this mapping, the molecular surfaces must be oriented for maximum geometric coincidence, as described above, and each inhibitor molecule is mapped onto the transition state. For each point on the transition state surface the spatially closest point on the inhibitor surface is found and the electrostatic potential of that inhibitor point is assigned the coordinates of that transition state point. Therefore the transition state, substrate, and inhibitors are all represented by the same geometrical surface, that of the transition state. However, the electrostatic potentials on these surface points defining a particular molecule are derived by the projection of the electrostatic potentials of that original molecular surface. After the molecules are described with the same geometry, input vectors are created with only the electrostatic potential information, ignoring the positional information since it is now the same for all molecules. This mapping ensures that similar regions on different molecules enter the same part of the neural network. This mapping assumes that the shape of the transition state is matched by the cavity at the active site. This cavity is responsible for formation of the transition state. The value of this approach will be shown a posteriori by the results.

Each data point in the input—that is, each discrete point chosen on the van der Waals surface at which the electrostatic potential is evaluated—enters the neural network through a discrete neuron. The network is composed of many simple neurons acting in parallel. The network function is determined by the interaction between these neurons. Networks "learn" by adjusting the strength of interaction between the neurons. The network has an input layer, a hidden layer, and an output layer. In the input layer, each input neuron corresponds to an input datum (in this case, a point on the van der Waals surface and the associated electrostatic potential or a deviation of a geometric location from a reference surface). There is complete interconnection between all neurons in adjacent layers, and the strength of interconnection is what is varied in training of the network.

The network used in the present invention was a feed forward network with back propagation of error that learns with momentum. Training of the network is accomplished by repeated back propagation of error throughout the network. Each iteration involves the introduction of an input and an output pattern, calculation of error, and readjustment of internal parameters called weights and biases. A generalization of the Widrow-Hoff learning rule was used to modify interconnection weights until presentation of the network with an electrostatic potential input pattern resulted in output of a known binding free energy. After the network is trained, it may be presented with an unknown pattern and it will mathematically generalize to produce an output binding free energy. The number of input patterns required to train a network varies with the input data; however, as reported below, between 4 and 7 training inhibitors were sufficient to allow a neural network to produce accurate predictions for unknown inhibitors. Few input substrates are required because each input contains hundreds of data points, and therefore a great deal of information. The small number of input substrates is remarkable from a mathematical perspective, and makes the method very practical to use.

Figure 3:
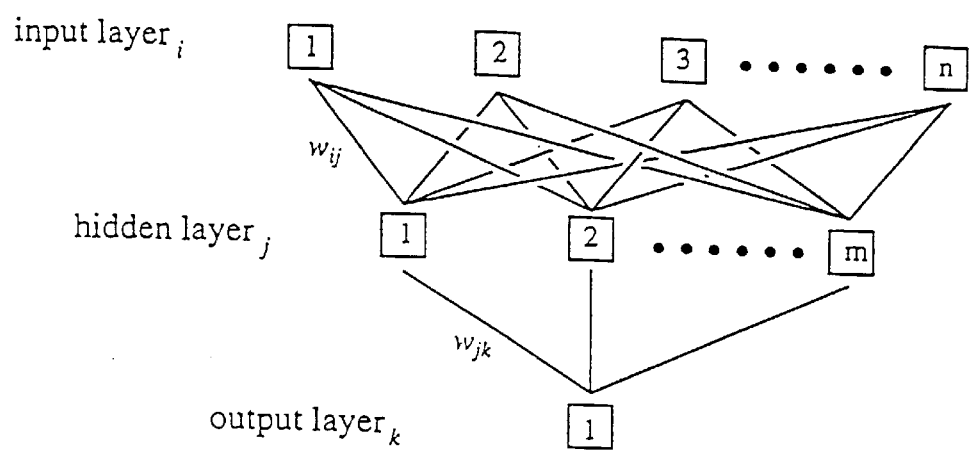
FIG. 3 shows a schematic diagram of the neural network employed in the method of the present invention.

The basic construction of a back propagation neural network has three layers: an input layer, hidden layer, and an output layer (FIG. 3). The input layer is where the different input vectors are transferred. The link between the layers of the network is one of multiplication by a weight matrix, where every entry in the input vector is multiplied by a weight and sent to every hidden layer neuron, so that the hidden layer weight matrix has the dimensions n by m, where n is the length of the input vector and m is the number of hidden layer neurons. A bias is added to the hidden and output layer neurons, which scales all the arguments before they are input into the transfer function. The hidden layer input $h^I_j$ for neuron j is calculated, $$h_j^I = b_j + \sum_{i=1}^{n} i_i^o w_{ij}$$

where $i_i^o$ is the output from the $i^{th}$ input neuron, $w_{ij}$ is the element of the weight matrix connection input from neuron i with hidden layer neuron j, and $b_j$ is the bias on the hidden layer neuron j. This vector $h_j^I$ is sent through a transfer function, f This function is nonlinear and usually sigmoidal, taking any value and returning a number between −1 and 1. A typical example is:

$$f(h_j^I) = \frac{1}{1 + e - h_j^I} - 1 = h_j^o$$

The hidden layer output, $h_j^o$ is then sent to the output layer. The output layer input $o_k^I$ is calculated for the $k^{th}$ output neuron $$o_k^I = b_k + \sum_{j=1}^{m} h_j^o w_{jk}$$

where $w_{jk}$ is the weight matrix element connecting hidden layer neuron j with output layer neuron k. The output layer output, $o_k^o$ is calculated with the same transfer function given above.

Referring to FIG. 3, the input layer is represented by the squares at the top of the diagram. The weights are represented by the lines connecting the layers: $w_{ij}$ is the weight between the $i^{th}$ neuron of the input layer and $j^{th}$ neuron of the hidden layer and $w_{jk}$ is the weight between the $j^{th}$ neuron of the hidden layer and the $k^{th}$ neuron of the output layer. In this diagram the output layer has only one neuron because the target pattern is a single number—the free energy of binding. Only a single output neuron is needed if the target for each input vector is a single number.

Back propagation was created by a generalization of the Widrow-Hofflearning rule applied to multiple-layer networks and nonlinear differentiable transfer functions (Rumelhart et al., *Parallel Distributed Processing*, Vol. 1, MIT Press, 1986). Input vectors and the corresponding output vectors are used to train until the network can approximate a function. The strength of a back propagation neural network is its ability to form internal representations through the use of a hidden layer of neurons. For example, the 'exclusive or' problem demonstrates the ability of neural networks, with hidden layers, to form internal representations and to solve complex problems. Suppose we have four input pattens [(0,1) (0,0) (1,0) (1,1)] with output targets [1, 0, 1, 0], respectively. A perceptron or other single layer system would be unable to simulate the function described by these four input/output pairs. The only way to solve this problem is to learn that the two types of inputs work together to affect the output. In this case the least similar inputs cause the same output, and the more similar inputs have different outputs. The computational ability required to solve this problem is not unlike that required to find the best inhibitor when it does not look like the transition state. It is this inherent ability of neural networks to solve complex puzzles that makes them well conditioned for the task of simulating biological molecular recognition.

Experiments

We report a study of these techniques using a number of different enzyme systems with their respective transition states, substrates, and inhibitors. Many different neural network constructions were studied, and the best neural network architecture varies with the enzyme system. Variations in the number of hidden layer neurons often caused the greatest change in the ability of the network to learn, and between four and twelve hidden layer neurons were used. Changing the number of iterations between $5 \times 10^3$ and $1 \times 10^6$ also had an affect on the ability of a network to learn. The learning rate controls the rate of change of the weights and biases, affecting a network's ability to converge; values ranging between 0.1 and 0.5 were used. A momentum term between 0.8 and 0.9 increased the probability that the network will converge at the global error minimum instead of a local error minimum.

AMP Nucleosidase and Adenosine Deaminase

The success of the trained neural networks in predicting ΔG/RT for enzyme-inhibitor and enzyme-transition state interactions for AMP nucleosidase and adenosine deaminase are shown in Table 1. The second column reports the experimentally determined free energies of binding for the transition states, substrates, or inhibitors shown in the first column. In the third column, the measure $S_e$ is used to rank similarity to the transition states. The fourth column gives predictions of ΔG/RT based on the $S_e$ values of the molecules. For these calculations, the binding free energies of the transition states and of the substrates are defined by the experimental values. Predicted values of ΔG/RT based on the Se values for the inhibitors were made by linear extrapolation between the values for the transition states and the substrates.

The training procedure for the neural network for these two systems involved training the network with four patterns for each system. The number of hidden layer neurons, number of iterations, learning rate, and momentum were adjusted until the network output the binding energies of the four molecules in the training set with 98% accuracy. Once the network had learned the four patterns in the training set, it was used to predict a binding energy for the fifth molecule. These are the numbers listed in the fifth column of Table 1. For enzyme systems with few members in the training sets, the number of hidden layers, iterations, learning rate, and momentum that give the best predictions for the test molecules were optimized for the four patterns in each training set.

TABLE 1

| Enzyme/Molecule | ΔG/RT (experimental) | Se | ΔG/RT (Se) | ΔG/RT (neural network) |
|---|---|---|---|---|
| AMP Nucleosidase | | | | |
| transition state | −39 | 1.000 | −39 (0%) | −33 (15%) |
| formycin | −17 | 0.434 | −18 (6%) | −17 (0%) |
| aminopyrazolo pyrimidine ribonucleotide | −12 | 0.310 | −14 (17%) | −15 (25%) |
| tubercidin | −9.9 | 0.298 | −13 (36%) | −9.3 (6%) |
| AMP | −9.0 | 0.173 | −9.0 (0%) | −10 (11%) |
| Adenosine Deaminase | | | | |
| transition state | −39 | 1.000 | −39 (0%) | −29 (26%) |
| hydrated purine ribonucleoside | −29 | 0.765 | −27 (7%) | −29 (0%) |
| (R)-coformycin | −25 | 0.604 | −19 (24%) | −16 (36%) |
| 1,6-dihydropurine ribonucleoside | −12 | 0.677 | −23 (92%) | −14 (17%) |
| adenosine | −10 | 0.428 | −10 (0%) | −11 (10%) |

For AMP nucleosidase, the errors in ΔG/RT as predicted by Se are: 0.0 for the transition state (by construction), 1.0

(6%) for formycin, 2.0 (17%) for aminopyrazolo pyrimidine ribonucleotide, 3.1 (36%) for tubercidin, and 0.0 for AMP (again, by construction). For the neural network predictions the following errors are found: 6.0 (15%) for the transition state, 0.0 for formycin, 3.0 (25%) for the aminopyrazolo pyrimidine ribonucleotide, 0.6 (6%) for tubercidin, and 1.0 (11%) for substrate. For adenosine deaminase, the errors in $\Delta G/RT$ as predicted by Se are: 0.0 for the transition state (by construction), 2.0 (7%) for hydrated purine ribonucleoside, 6.0 (24%) for (R)-coformycin, 11.0 (92%) for 1,6-dihydropurine ribonucleoside, and 0.0 for adenosine (again, by construction).

For AMP nucleosidase, the errors in $\Delta G/RT$ as predicted by the neural network are: 6.0 (15%) for the transition state, 0.0 (0%) for fornycin, 3.0 (25%) for aminopyrazolo pyrimidine ribonucleotide, 0.6 (6%) for tubercidin, and 1.0 (11%) for AMP. For adenosine deaminase, the errors in $\Delta G/RT$ as predicted by the neural network are: 10.0 (26%) for the transitionstate, 0.0 (0%) for hydrated purine ribonucleoside, 9.0 (36%) for (R)-coformycin, 2.0 (17%) for 1,6-dihydropurine ribonucleoside, and 1.0 (10%) for adenosine.

For the three binding constants predicted by Se, the average error is 20% of the experimental $\Delta G/RT$ for AMP nucleosidase, and 41% for adenosine deaminase. Even for such a small training set, the error from Se is quite large in the case of adenosine deaminase, and this is mainly because 1,6-dihydroribonucleoside is not a good inhibitor. Without it, the average error is 15%.

The neural network, for the five predictions, performs with 11% error in $\Delta G/RT$ in the case of AMP nucleosidase, and 18% error in the case of adenosine deaminase. The neural network is poorer at predicting the transition state binding free energy for adenosine deaminase. Nonetheless, the average error over the five molecules in the adenosine deaminase series is only 18%. Both the neural network and the similarity measure have difficulty in predicting binding energy for (R)-coformycin, because its ring structure is sufficiently different from the other molecules of the training set.

Cytidine Deaminase

Figure 4:
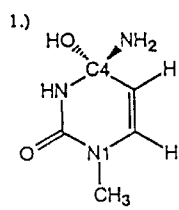
FIG. 4 shows the structures of the methyl derivatives of the molecules used in the cytidine deaminase experiments according to the present invention.
Figure 4:
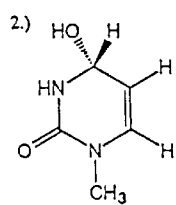
Figure 4:
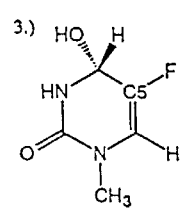
Figure 4:
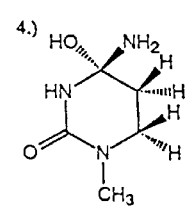
Figure 4:
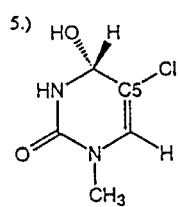
Figure 4:
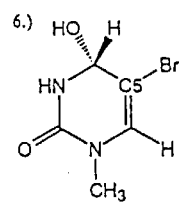
Figure 4:
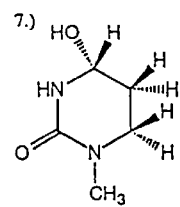
Figure 4:
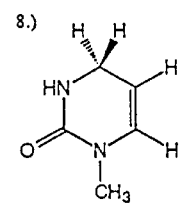
Figure 4:
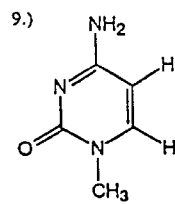
Figure 4:
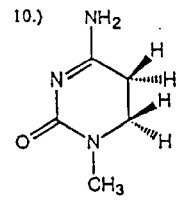
Figure 4:
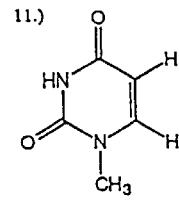
Figure 4:
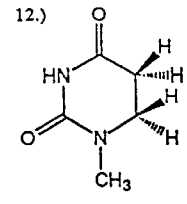

Cytidine deaminase catalyzes the hydrolysis of the amine group on cytidine to yield the products uridine and ammonia. Besides the transition state for the reaction and the substrate, there were 10 other compounds available in the literature for which binding free energies had been measured (Betts et al., J. Mol. Biol. 235:635–656 (1994); Frick et al., Biochemistry 28:9423–9430(1989); Horensteinetal., Biochemistry 32:7089–7097 (1993)). FIG. 4 shows the methyl derivatives (replacing the ribose ring) of the molecules used in these experiments. Methyl derivatives were used because the ribose moiety is unchanged in all 12 molecules and so this constant factor remained the same for all potential inhibitors. There is no transition state structure available for this molecule, but there is a crystal structure available for the enzyme complexed with the transition state analog 5-flouropyrimidin-2-one ribonucleoside, and this structure was used as a starting point for a transition state model. The reaction mechanism was assumed to be similar to that for adenosine deaminase. The C4 to O (of the attacking —OH) is constrained to be 1.67 Å, corresponding to that found in the crystal structure of the enzyme-inhibitor complex. The remainder of the molecule was energy minimized, using the GAUSSIAN 94 package as described above. In this case, because we employ the methyl derivatives of the molecules, conformation about flexible bonds was not a significant factor in the calculations.

There is another significant difference in the cytidine deaminase system with its more diverse set of inhibitors. In particular, the halogenated inhibitors represent a new challenge to the approach. In addition to changing the electrostatic features at the van der Waals surface, the halogen substituted inhibitors differ in size so significantly from the transition state reference surface that geometric information needs to be included to derive the best results from the neural network approach. In addition to electrostatic information, the neural network was presented with a second set of data which gives the deviation of the surface points from a reference molecule chosen to be large enough that all other molecules were contained within its volume (in particular, the 5-bromo substituted surface).

The success of the proposed methodology is demonstrated by the results shown in Table 2. Referring now to Table 2, the $\Delta G/RT$ values calculated by the neural network are shown using 7 and 11 molecules to train the network. In the case of 7 molecules, an actual experiment was simulated by choosing five molecules to leave out of the training set. These molecules were chosen without regard to chemical structure, but rather were chosen to span the range of binding free energy. Of these five, one was chosen randomly to design the neural network architecture (i.e., the network's adjustable parameters—number of hidden layer neurons, learning rate, momentum, and number of learning iterations). These parameters were adjusted so that the approach could accurately predict the known binding free energy of the target molecule. No further adjustment to the network was made beyond this stage. Finally this trained network was used to predict the binding free energies of the remaining four unknown molecules. As Table 2 shows, the approach is able to predict the binding free energies, and is even able to yield reasonable results when trained with only 7 known experimental values, and when the network is optimized to predict the binding free energy of a randomly chosen molecule.

TABLE 2

| Molecule | $\Delta G/RT$ (experimental) | $\Delta G/RT$ $S_e$ | ($S_e$) | $\Delta G/RT$ (neural network) 7 | 11 |
|---|---|---|---|---|---|
| transition state | −36 | 1.00 | −36 (0%) | | −30 (20%) |
| hydrated pyrimidine-2-one ribonucleoside | −27 | 0.87 | −30 (11%) | −26 (4%) | −27 (0%) |
| hydrated 5-fluoro-pyrimidine-2-one ribonucleoside | −24 | 0.78 | −26 (8%) | | −19 (21%) |
| transition state for 5,6-dihydrocytidine | −21 | 0.88 | −30 (43%) | | −23 (9%) |
| hydrated 5-chloro-pyrimidine-2-one ribonucleoside | −19 | 0.70 | −22 (16%) | −18 (5%) | −19 (0%) |
| hydrated 5-bromo-pyrimidine-2-one ribonucleoside | −18 | 0.68 | −21 (17%) | | −17 (6%) |
| 3,4,5,6-tetrahydrouridine | −16 | 0.76 | −25 (56%) | | −15 (6%) |
| 3,4-dihydrozebularine | −10 | 0.68 | −22 (120%) | −13 (30%) | −12 (20%) |
| cytidine | −9.9 | 0.39 | −9.9 (0%) | | −8.3 (16%) |
| 5,6-dihydrocytidine | −9.1 | 0.28 | −5.3 (42%) | | −7.5 (18%) |
| uridine | −6.0 | 0.58 | −18 (200%) | −9.9 (74%) | −6.1 (2%) |
| 5,6-dihydrouridine | −5.7 | 0.45 | −12 (111%) | | −6.2 (9%) |

Nitric Oxide Synthetase

To further test our approach, we have also investigated inhibitors for two different isoforms of nitric oxide synthetase (NOS). There has been an explosion of interest in recent years in the biological importance of NO, and its synthesis in living systems. The two isoforms studied are the brain isoform (hereinafter "bNOS") and the inducible, $Ca^{2+}$-independent isoform (hereinafter "iNOS"). These isoforms have very different roles under different biomedical scenarios. For example, overproduction of NO by bNOS during stroke has been implicated in cell death, and overproduction of iNOS has been implicated in circulatory shock and excess inflammation. Consequently, selective inhibition of either isoform as appropriate would have significant potential medical benefits. In addition, potential inhibitors of NOS vary widely in chemical structure (FIG. 5).

Four specific challenges are presented to the method of the present invention by the NOS system. First, the great diversity in geometry of the inhibitors forces the method to show if widely variable geometric and electrostatic structures can all be handled by the same neural construction. Second, the NOS reaction is known to be an extraordinarily complex biochemical reaction, and so provides a rigorous test of the claim that predictions of binding free energies can be made by examining the quantum properties of substrate or inhibitor molecules. Third, most of the molecules we study are linear chain molecules, predominantly connected by single bonds between atoms, and so have a high degree of conformational flexibility. This system provides a convincing test of the ability of the method to predict binding in such conformationally flexible systems when all molecules are held in an extended conformation. Fourth, we have data available on a relatively large set of inhibitors for two different isoforms which not only exhibit quantitatively different binding energies, but qualitatively different binding patterns (i.e., the order of binding free energies shifts from one isoform to the other).

Figure 5:
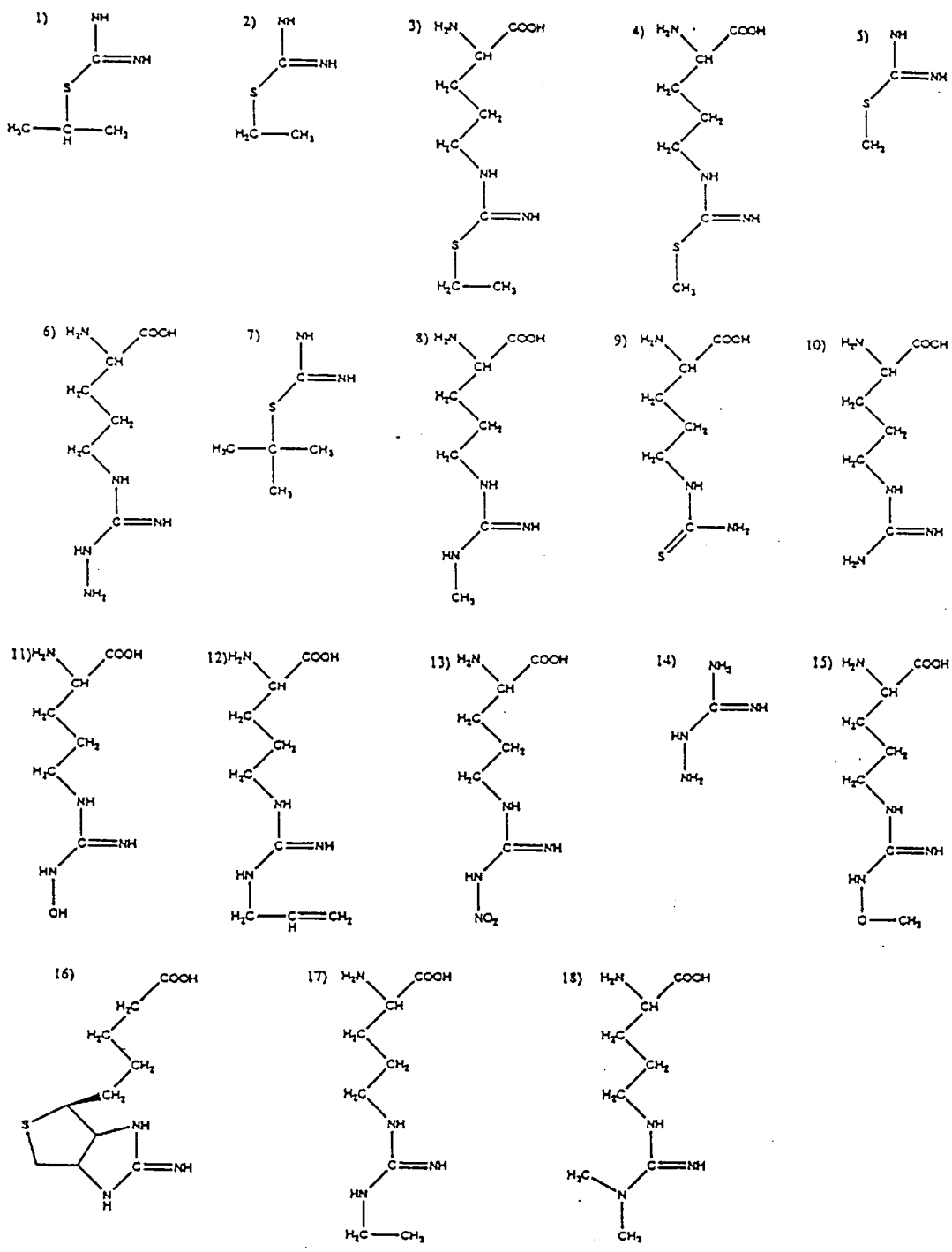
FIG. 5 shows the structures of the potential inhibitors used in the NOS experiments according to the present invention.

Referring to FIG. 5, the 18 molecules studied vary widely in structure, and in cases where clearly only the guanidino group was present (or similarly an isothiourea), the central carbon atom was aligned with the guanidino carbon of the arginine analogues. As in the cytidine deaminase study, a set of 12 randomly chosen molecules was used in the training set, along with a molecule with a known binding energy to optimize the construction of the neural network. Then, the free energies of binding for the five remaining molecules were calculated.

In each case, two sets of data are presented which represent two different choices of molecules for which predictions must be generated. In the second set molecule number 16, the biotin derivative, was included in the prediction set because it is very different from the other molecules in the training set, and we felt it would be a strong test of the algorithm. The results for iNOS are shown in Table 3, and those for bNOS are shown in Table 4.

TABLE 3

| Molecule (from FIG. 5) | ΔG/RT (experimental) | ΔG/RT (prediction #1) | ΔG/RT (prediction #2) |
| --- | --- | --- | --- |
| 1 | −18.44 | | −16.68 |
| 2 | −17.78 | −18.08 | |
| 3 | −17.73 | | |
| 4 | −17.03 | | −15.22 |
| 5 | −15.94 | | |
| 6 | −13.28 | −11.90 | |
| 7 | −12.94 | | |
| 8 | −12.90 | | −10.17 |
| 9 | −12.53 | | |
| 10 | −12.21 | −10.75 | |

TABLE 3-continued

| Molecule (from FIG. 5) | ΔG/RT (experimental) | ΔG/RT (prediction #1) | ΔG/RT (prediction #2) |
| --- | --- | --- | --- |
| 11 | −11.88 | | |
| 12 | −11.68 | | −11.36 |
| 13 | −11.65 | | |
| 14 | −11.04 | −12.84 | |
| 15 | −10.80 | | |
| 16 | −10.74 | | −12.88 |
| 17 | −9.42 | | |
| 18 | −8.11 | −11.05 | |
| average deviation: | | 1.58 | 1.75 |

TABLE 4

| Molecule (from FIG. 5) | ΔG/RT (experimental) | ΔG/RT (prediction #1) | ΔG/RT (prediction #2) |
| --- | --- | --- | --- |
| 3 | −21.42 | | −16.26 |
| 4 | −20.54 | −18.39 | |
| 2 | −17.36 | | |
| 1 | −17.11 | | −13.84 |
| 9 | −16.63 | | |
| 5 | −15.65 | −14.75 | |
| 13 | −15.42 | | |
| 7 | −14.29 | | −13.55 |
| 8 | −14.17 | | |
| 12 | −13.98 | −14.01 | |
| 6 | −13.63 | | |
| 10 | −12.50 | | −10.81 |
| 15 | −12.02 | | |
| 11 | −11.09 | −11.08 | |
| 16 | −10.19 | | −11.30 |
| 17 | −9.63 | | |
| 18 | −8.11 | | |
| 14 | −7.09 | −9.75 | |
| average deviation: | | 1.15 | 2.41 |

The data for iNOS are fairly uniform, with an average deviation of 1.58 and 1.75 dimensionless energy units. This level of accuracy is very surprising, given the complexity of the enzymatic reaction being tested. Furthermore, the data support the application of this method to highly variable and flexible molecules with minimal information about binding. The data for bNOS show slightly less absolute accuracy, but because the brain isoform binds inhibitors more tightly than iNOS, the relative error is only about 16%, even in the worst case. The range of binding energies is greater than 10 dimensionless energy units for iNOS and 14.5 dimensionless energy units for bNOS, so even with this highly variable and flexible set of inhibitor molecules, the results are accurate to within about 15% of the binding energy range.

IU-Nucleoside Hydrolase

Figure 7:
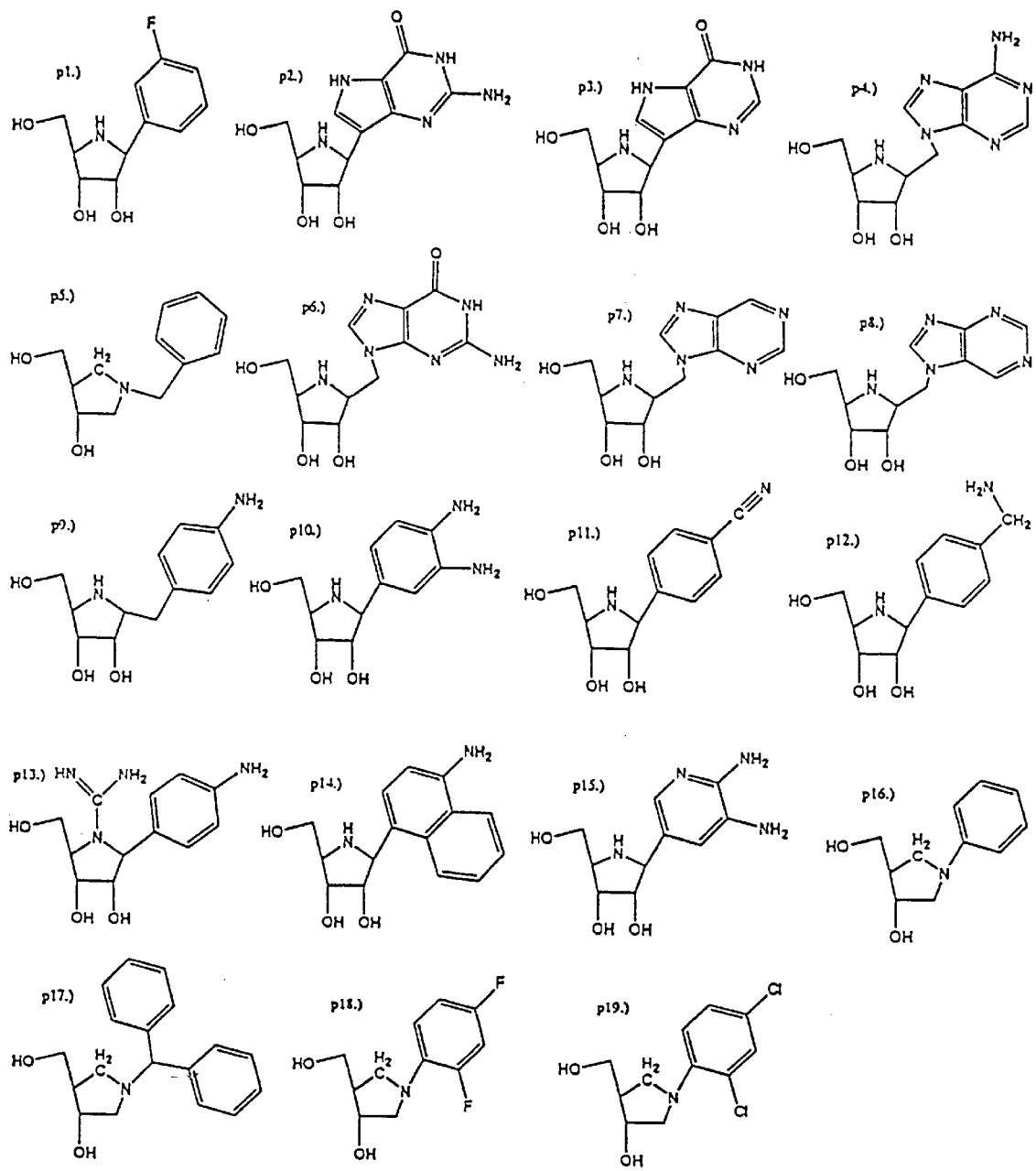
FIG. 7 shows the structures of the potential inhibitors of IU-hydrolase whose binding constants were determined according to the present invention.

The IU-nucleoside hydrolase system is involved in purine salvage by parasites from hosts. The enzyme was studied for two reasons. First, the mechanism of this enzyme is known to be very similar to that of the enzymatic subunit of cholera toxin. Inhibitors of IU-nucleoside hydrolase are not inhibitors of cholera toxin, due to the presence of a dinucleotide as opposed to a mononucleotide. However, the ability to predict binding patterns in inhibitors of the IU-nucleoside hydrolase will permit the identification of possible variants of these inhibitors for testing as cholera toxin inhibitors. Second, the existence of a large group of recently synthesized but uncharacterized inhibitors allowed a realistic test of the method (see FIG. 7).

Figure 6:
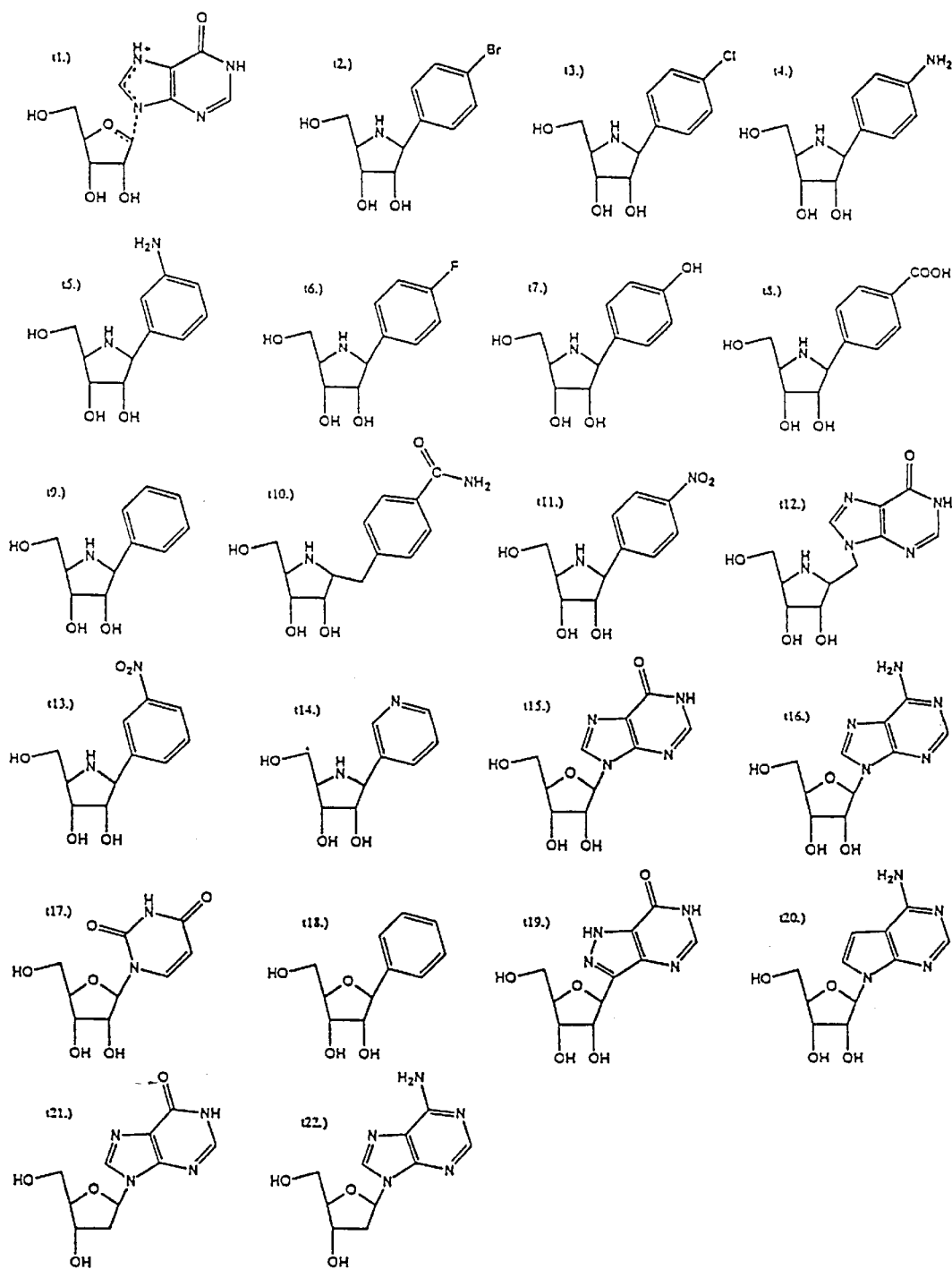
FIG. 6 shows the structures of the known inhibitors of IU-hydrolase used to train he neural network according to the present invention.

To train the neural network, an older set of 22 inhibitors of known binding free energy was used (FIG. 6). The binding constants of the molecules shown in FIG. 7 were then calculated, and the results are presented in Table 5. Accurate binding free energies could not be calculated for molecules which bind more weakly than Ki=50 μM. Therefore, for several molecules, the experimental analysis could only show that the molecules bound at an absolute value less than 9.81 dimensionless units. However, the remainder of the data are in good agreement with the experimental data, with the worst errors being about 15%. These results illustrate the utility of the method of the invention for identifying strong binders deserving of further study (i.e., those having ΔG/RT values less than −14) from weak binders.

TABLE 5

| Molecule | ΔG/RT (experimental) | ΔG/RT (predicted) |
| --- | --- | --- |
| p1.) | −14.7 | −14.0 |
| p2.) | −15.9 | −14.1 |
| p3.) | −17.3 | −16.8 |
| p4.) | −10.7 | −10.2 |
| p5.) | ≥−9.81 | −11.2 |
| p6.) | −10.8 | −9.98 |
| p7.) | ≥−9.81 | −7.06 |
| p8.) | ≥−9.81 | −6.49 |
| p9.) | −10.8 | −8.94 |
| p10.) | −15.9 | −17.1 |
| p11.) | −15.11 | −17.1 |
| p12.) | −14.4 | −16.5 |
| p13.) | ≥−9.81 | −12.5 |
| p14.) | −14.8 | −16.5 |
| p15.) | −14.8 | −17.1 |
| p16.) | ≥−9.81 | −8.80 |
| p17.) | ≥−9.81 | −8.20 |
| p18.) | ≥−9.81 | −8.08 |
| p19.) | ≥−9.81 | −7.09 |

The high level of predictive accuracy of neural networks makes it interesting to study how networks discriminate between different regions on the electrostatic potential surface of inhibitor molecules. The evident accuracy of the method is due to the use of the entire three dimensional surface of the molecule, rather than a collapsed representation. The weights in the hidden layer associated with regions of the input electrostatic surfaces that are important in binding have large absolute values. The network is presented with an input pattern and an output pattern. To minimize the error, the network must recognize regions that change and affect the binding energy relative to those regions that change and do not affect binding energy. This recognition occurs when the neural network's weights are adjusted so that important regions are multiplied by large weights and unimportant regions are multiplied by small weights. Documentation of this behavior is made by inspection of the absolute values of every number in the hidden-layer weight matrix of a trained network. The matrix is collapsed into a vector $V_i$ by summing on j where j=j, . . . , m and m is the number of hidden layer neurons:

$$V_i = \sum_{j=1}^{m} |w_{ij}|$$

and where "i" refers to the input surface points. Large values for $V_i$ represent regions found to be important to the neural network, and small values represent regions found to be unimportant. Since all the patterns were generated by mapping the electrostatic potential of different molecules onto the transition state surface, the common transition state geometry is used to identify those regions on the molecules found as most important by the neural net. This can be represented by, for example, coloring points on a van der Waals surface with large $V_i$ values one color and regions with small values another color. Regions on molecular surfaces with intermediate weights have a mixture of the two colors. The network is not only able to identify regions in the training set that strengthen binding, it can also ignore regions that change without affecting binding.

The entire molecular electrostaticpotential surfaces of the inhibitors, substrates, and experimentally determined transition states can be used to train neural networks to accurately predict binding energies of proposed inhibitor molecules. The neural network method possesses the ability to adjust a model of the system defined by a relatively small number of structure affinity pairs. Our calculations show the ability of the method to predict an enzyme's affinity to inhibitor molecules when minimal information about the enzymatic active site is provided.

The predictive power extends to the tightly bound transition state when the network is trained with less tightly bound inhibitors. Similar methods have been used by other groups for the task of simulating molecular recognition, but the present work is the first that uses the entire electrostatic potential surfaces of the molecules as the inputs to a back propagation neural network. Our surface transformation has some similarity with the procedure of Gasteiger et al. where Kohonen self-organizing networks were used to transform different 3-dimensional surfaces to a plane. The work of Wagener et al. reduces the molecular electrostatic potential surfaces for each molecule onto twelve autocorrelation coefficients. Importantly, these methods necessarily reduce the amount of information being used for prediction. Wagener et al. report an investigation of the binding affinity between 32 molecules and a receptor site. Because these molecules are constructed with similar steroid backbones, there is no confusion as to how to orient the molecules with respect to each other. The present method can be applied to this system as well. Tetko et al used a similar approach to that used by Wagner et al. They devised a protocol that can be used to describe the structural features of molecules with a small set of coefficients. These sets of coefficients were used as inputs to a neural network.

Previous work with similarity measures give equal weight to all the regions of the molecular surfaces while neural networks become sensitive to certain regions and less sensitive to others. Enzyme-substrate binding occurs through a number of specific interactions that do not cover the entire molecular surface. Binding energy is not always a linear function of similarity to the transition state. Neural networks can also learn to recognize regions of inhibitors likely to be chemically modified by an enzyme. The neural network method is well suited for the task of simulating biological molecular recognition. Such methods can be used to search chemical libraries to augment the process of discovering pharmacological transition state inhibitors.

It would be appreciated by those in the art that in addition to the electrostatic potential, other parameters descriptive of interactions between enzymes and substrates or inhibitors, and between receptors and ligands, could be utilized advantageously in the present method. These could include, for example, hydrophobic interactions, polarization effects, steric effects, and geometric effects. It would also be appreciated by those in the art that the present method can be encoded as information on a medium readable by a general-purpose computer to enable a computer to perform the necessary calculations.

All patents and references mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for determining a free energy of binding of a potential transition-state inhibitor to an enzyme, comprising the steps of:

obtaining a structure and a free energy of binding to said enzyme for each of two or more enzyme substrates or inhibitors;

orienting said structures of said two or more enzyme substrates or inhibitors for maximum geometric coincidence with each other;

determining an electrostatic potential at each of more than one point on a van der Waals surface of each of said enzyme substrates or inhibitors;

thereafter, mapping each of said electrostatic potentials of each of said enzyme substrates or inhibitors onto a geometric surface of one of said two or more enzyme substrates or inhibitors, each of said two or more enzyme substrates or inhibitors being thereby described by an identical surface geometry but a different electrostatic potential surface, and each of said electrostatic potentials being described by positional information relating said electrostatic potentials to said geometric surface;

thereafter, inputting said electrostatic potentials, said positional information, and said known free energy of binding of one of said two or more enzyme substrates or inhibitors into a neural network;

thereafter, training said neural network until said neural network predicts said free energy of binding of said one of said two or more enzyme substrates or inhibitors;

repeating said steps of inputting and training for each of the remaining said two or more enzyme substrates or inhibitors to produce a trained network;

thereafter, determining a potential transition-state inhibitor electrostatic potential at each of more than one point on a van der Waals surface of said potential transition-state inhibitor, said potential transition-state inhibitor having a known structure and an unknown free energy of binding to said enzyme;

orienting said structure of said potential transition-state inhibitor for maximum geometric coincidence with said structures of said two or more enzyme substrates or inhibitors;

thereafter, mapping each of said electrostatic potentials of said potential transition-state inhibitor onto a geometric surface of one of said two or more enzyme substrates or inhibitors, said potential transition-state inhibitor having a surface geometry identical to that of said two or more enzyme substrates or inhibitors, but a different electrostatic potential surface, and each of said electrostatic potentials of said potential transition-state inhibitor being described by positional information relating said electrostatic potentials to said geometric surface; thereafter, inputting said electrostatic potentials and said positional information of said electrostatic potentials of said potential transition-state inhibitor into said trained network; and using said trained network to calculate a free energy of binding of said potential transition-state inhibitor to said enzyme;

wherein said neural network contains an input layer, a hidden layer, and an output layer, and is a feed forward network with back propagation of error that learns with momentum; wherein the network uses between 4 and 12 hidden layer neurons, a learning rate between 0.1 and 0.5, a momentum term between 0.8 and 0.9, and between $5 \times 10^3$ and $1 \times 10^6$ learning iterations; and wherein the number of hidden layer neurons, number of iterations, learning rate, and momentum can be adjusted so that the network outputs a binding energy with 98% accuracy.

2. A computer readable medium, comprising:

computer-readable information;

said information capable of interacting with a computer to produce an output;

said output being a calculated free energy of binding of a potential transition-state inhibitor to an enzyme;

said output being calculated by:

orienting structures of two or more enzyme substrates or inhibitors for maximum geometric coincidence with each other;

each of said two or more enzyme substrates or inhibitors having a predetermined structure and a predetermined free energy of binding to said enzyme;

determining an electrostatic potential at each of more than one point on a van der Waals surface of each of said enzyme substrates or inhibitors;

thereafter, mapping each of said electrostatic potentials of each of said enzyme substrates or inhibitors onto a geometric surface of one of said two or more enzyme substrates or inhibitors, each of said two or more enzyme substrates or inhibitors being thereby described by an identical surface geometry but a different electrostatic potential surface, and each of said electrostatic potentials being described by positional information relating said electrostatic potentials to said geometric surface;

thereafter, inputting said electrostatic potentials, said positional information, and said known free energy of binding of one of said two or more enzyme substrates or inhibitors into a neural network;

thereafter, training said neural network until said neural network predicts said free energy of binding of said one of said two or more enzyme substrates or inhibitors;

repeating said steps of inputting and training for each of the remaining said two or more enzyme substrates or inhibitors to produce a trained network;

thereafter, determining a potential transition-state inhibitor electrostatic potential at each of more than one point on a van der Waals surface of said potential transition-state inhibitor, said potential transition-state inhibitor having a known structure and an unknown free energy of binding to said enzyme;

orienting said structure of said potential transition-state inhibitor for maximum geometric coincidence with said structures of said two or more enzyme substrates or inhibitors;

thereafter, mapping each of said electrostatic potentials of said potential transition-state inhibitor onto a geometric surface of one of said two or more enzyme substrates or inhibitors, said potential transition-state inhibitor having a surface geometry identical to that of said two or more enzyme substrates or inhibitors, but a different electrostatic potential surface, and each of said electrostatic potentials of said potential transition-state inhibitor being described by positional information relating said electrostatic potentials to said geometric surface;

thereafter, inputting said electrostatic potentials and said positional information of said electrostatic potentials of said potential transition-state inhibitor into said trained network; and using said trained network to calculate a free energy of binding of said potential transition-state inhibitor to said enzyme;

wherein said neural network contains an input layer, a hidden layer, and an output layer, and is a feed forward network with back propagation of error that learns with momentum; wherein the network uses between 4 and 12 hidden layer neurons, a learning rate between 0.1 and 0.5, a momentum term between 0.8 and 0.9, and between $5 \times 10^3$ and $1 \times 10^6$ learning iterations; and wherein the number of hidden layer neurons, number of iterations, learning rate, and momentum can be adjusted so that the network outputs a binding energy with 98% accuracy.

* * * * *